United States Patent
Gauvry et al.

(10) Patent No.: US 8,367,682 B2
(45) Date of Patent: Feb. 5, 2013

(54) PYRIMIDINE DERIVATIVES AND THEIR USE AS PESTICIDES

(75) Inventors: Noëlle Gauvry, Kembs-Loechle (FR); François Pautrat, Mulhouse (FR); Jacques Bouvier, Neuchâtel (CH); Jörg Früchtel, Lörrach (DE); Beatrice Bapst, St-Aubin (FR); Sandra Schorderet Weber, Neuchâtel (CH)

(73) Assignee: Novartis AG, Basel (CH)

( * ) Notice: Subject to any disclaimer, the term of this patent is extended or adjusted under 35 U.S.C. 154(b) by 629 days.

(21) Appl. No.: 12/373,559

(22) PCT Filed: Jul. 17, 2007

(86) PCT No.: PCT/EP2007/057395
§ 371 (c)(1),
(2), (4) Date: Aug. 24, 2009

(87) PCT Pub. No.: WO2008/009691
PCT Pub. Date: Jan. 24, 2008

(65) Prior Publication Data
US 2010/0010003 A1 Jan. 14, 2010

(30) Foreign Application Priority Data
Jul. 21, 2006 (EP) .................................. 06117639

(51) Int. Cl.
*A01N 43/54* (2006.01)
*C07D 239/52* (2006.01)
(52) U.S. Cl. ...................................... 514/269; 544/319

(58) Field of Classification Search ................. 514/269; 544/319
See application file for complete search history.

(56) References Cited

U.S. PATENT DOCUMENTS
5,707,995 A 1/1998 Munro et al.
6,342,499 B1 1/2002 Black et al.

FOREIGN PATENT DOCUMENTS
WO WO 00/49001 8/2000
WO WO 2005/058802 6/2005
WO WO 2005/085211 9/2005

*Primary Examiner* — Kortney L Klinkel
(74) *Attorney, Agent, or Firm* — Ann R. Pokalsky, Esq.; Dilworth & Barrese, LLP

(57) ABSTRACT

The invention relates to new pyrimidine compounds of formula (1) wherein the variables have the meaning as indicated in the claims; in free form and in salt form; and optionally the enantiomers and geometrical isomers thereof. The compounds of formula (1) are useful in the control of parasites, in particular ectoparasites, in and on warmblooded animals.

6 Claims, No Drawings

PYRIMIDINE DERIVATIVES AND THEIR USE AS PESTICIDES

RELATED APPLICATION

This application claims priority to PCT Application Number PCT/EP2007/057395, filed Jul. 17, 2007, which claims priority to EPO Application Number 06117639.2, filed Jul. 21, 2006, entitled "Pyrimidine Derivatives And Their Use As Pesticides", each herein incorporated by reference.

The present invention relates to novel 2,4,6-trisubstituted 5-aminopyrimidine compounds, processes for their manufacture, their use in the control of ectoparasites, especially insects and acari, on non-human animals, especially productive livestock and domestic animals, and furthermore pesticidal compositions which contain one or more of these compounds.

WO 2005/85211 discloses a large group of 4,6-bis-phenoxy-5-amino-pyrimidines with various substituents in the 2 position, among them 4,6-bis-(4-fluoro-3-[trifluoromethyl]-phenoxy)-5-aminopyrimidine which is substituted in the 2-position by phenyl. The biological properties, in particular the effectiveness against ectoparasites, of this compound are, however, dissatisfactory in the field of pest control. Accordingly, there is a need to find further compounds with improved pesticidal properties, especially for the control of ectoparasites. It now has been surprisingly found that 4,6-bis-(4-halogeno-3-[trifluoromethyl]phenoxy)-5-aminopyrimidines with a heterocyclic or substituted phenyl substituent in the 2-position, have superior properties in the control of ectoparasites.

The present invention therefore in one aspect relates to a compound of formula

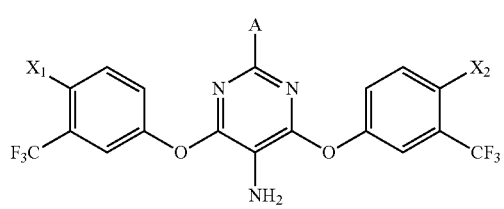

(I)

wherein $X_1$ and $X_2$ are each independently halogen; and A is a radical of formula

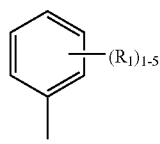

(2)

wherein $(R_1)_{1-5}$ is 1 to 5 same or different substituents selected from the group consisting of $C_1$-$C_4$-alkyl, halogen-$C_1$-$C_4$-alkyl, hydroxy-$C_1$-$C_4$-alkyl, $C_1$-$C_4$-alkoxy-$C_1$-$C_4$-alkyl, $R_2R_3N$—$C_1$-$C_4$-alkyl, halogen, cyano, hydroxy, $C_1$-$C_4$-alkoxy, halogen-$C_1$-$C_4$-alkoxy, thiol, $C_1$-$C_4$-alkylthio, halogen-$C_1$-$C_4$-alkylthio, $C_1$-$C_4$-alkanoyl, halogen-$C_1$-$C_4$-alkanoyl, $C_1$-$C_4$-alkanoylamino, halogen-$C_1$-$C_4$-alkanoylamino, $COOR_2$, $CONH_2$, $CONR_2R_3$, $SO_3H$, $SO_2NR_2R_3$, $C_1$-$C_4$-alkyl-sulfonylamino, $C_1$-$C_4$-alkylsulfonyloxy, halogen-$C_1$-$C_4$-alkylsulfonyloxy, $C_1$-$C_4$-alkylsulfonyl, halogen-$C_1$-$C_4$-alkylsulfonyl, $C_1$-$C_4$-alkylsulfinyl, halo-$C_1$-$C_4$-alkylsulfinyl, $NR_2R_3$ and a $C_3$-$C_5$-heterocyclic radical having 1 or 2 same or different hetero-atoms selected from O, S and N; or A is a radical of formula

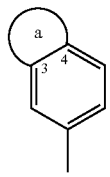

(3)

wherein ring (a) denotes a 5- or 6-membered carbocyclic or heterocyclic ring which is annulated in the 3- and 4-position; or A is a heterocyclic radical having from 3 to 9 C-atoms and from 1 to 3 same or different heteroatoms selected from the group consisting of N, O and S, which heterocyclic radical is unsubstituted or further substituted by $C_1$-$C_4$-alkyl, hydroxy, $C_1$-$C_4$-alkoxy, halogen or $NR_2R_3$; and $R_2$ and $R_3$ are each independently hydrogen or $C_1$-$C_4$-alkyl which is unsubstituted or substituted by halogen, hydroxy, $C_1$-$C_4$-alkoxy, thiol or $C_1$-$C_4$-alkylthio, in free form or in salt form.

A further embodiment of the present invention relates to compounds of the above formula (1), wherein $X_1$ and $X_2$ are as defined above, A is a radical of the formula (2) given above, and $(R_1)_{1-5}$ is 1 to 5 same or different substituents selected from the group consisting of $C_1$-$C_4$-alkyl, halogen-$C_1$-$C_4$-alkyl, hydroxy-$C_1$-$C_4$-alkyl, $C_1$-$C_4$-alkoxy-$C_1$-$C_4$-alkyl, $R_2R_3N$—$C_1$-$C_4$-alkyl, halogen, cyano, nitro, hydroxy, $C_1$-$C_4$-alkoxy, halogen-$C_1$-$C_4$-alkoxy, thiol, $C_1$-$C_4$-alkylthio, halogen-$C_1$-$C_4$-alkylthio, $C_1$-$C_4$-alkanoyl, halogen-$C_1$-$C_4$-alkanoyl, $C_1$-$C_4$-alkanoylamino, halogen-$C_1$-$C_4$-alkanoylamino, $COOR_2$, $CONH_2$, $CONR_2R_3$, $SO_3H$, $SO_2NR_2R_3$, $C_1$-$C_4$-alkylsulfonylamino, $C_1$-$C_4$-alkylsulfonyloxy, halogen-$C_1$-$C_4$-alkylsulfonyloxy, $C_1$-$C_4$-alkylsulfonyl, halogen-$C_1$-$C_4$-alkylsulfonyl, $C_1$-$C_4$-alkylsulfinyl, halo-$C_1$-$C_4$-alkylsulfinyl, $NR_2R_3$ and a $C_3$-$C_5$-heterocyclic radical having 1 or 2 same or different hetero-atoms selected from O, S and N; and $R_2$ and $R_3$ are each as defined above.

Alkyl—as a group per se and as structural element of other groups and compounds such as halogen-alkyl, hydroxyl-alkyl, alkoxy-alkyl, $R_2R_3N$-alkyl, alkoxy, alkylthio, alkylsulfinyl, alkylsulfonyl or alkylsulfonyloxy alkylsulfonylamino—is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl. Preferred meanings of alkyl are methyl, ethyl or n- or isopropyl, in particular $C_1$-$C_2$-alkyl and especially methyl or ethyl.

Alkoxy—as a group per se and as structural element of other groups—is for example methoxy, ethoxy, propoxy, isopropoxy, n-butoxy, isobutoxy, sec.-butoxy or tert.-butoxy; preferably $C_1$-$C_2$-alkoxy, and especially methoxy or ethoxy.

Halogen—as a group per se and as structural element of other groups—preferably means, for example, iodine, bromine, chlorine or fluorine, preferably chlorine or fluorine.

Halogen-substituted carbon-containing groups and compounds, such as halogen-alkyl, halogen-$C_1$-$C_4$-alkoxy, halogen-$C_1$-$C_4$-alkylthio, halogen-$C_1$-$C_4$-alkanoyl, halogen-$C_1$-$C_4$-alkanoylamino, halogen-$C_1$-$C_4$-alkylsulfonyloxy or halogen-$C_1$-$C_4$-alkylsulfonyl, may be partially halogenated or perhalogenated, whereby in the case of multiple halogenation, the halogen substituents may be identical or different. Examples of preferred halogen-alkyl—as a group per se and as structural element of other groups and compounds such as halogen-alkoxy or halogen-alkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted once to eleven times by fluorine, chlorine and/or bromine, such as $CF(CF_3)(CHF)_2CF_3$ or $CH_2(CF_2)_3CF_3$; and hexyl or one of its isomers substituted once to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Examples of alkanoyl—as a group per se and as structural element of other groups and compounds such as halogen-alkanoyl, alkanoylamino or halogen-alkanoylamino—are propionyl or in particular acetyl.

Examples of heterocyclic radicals or heterocyclic rings are thienyl, furanyl, pyrryl, pyrrolidinyl, dioxolanyl, oxazolyl, thiadiazolyl, oxadiazolyl, pyrazolyl, pirazinyl, piperazinyl, piperidinyl, morpholinyl, pyridyl, pyrimidyl, s-triazinyl, 1,2,4-triazinyl, imidazolyl, thiazolyl, triazolyl, tetrazolyl, benzothienyl, benzofuranyl, benzothiazolyl, benzoxazolyl, benzimidazolyl, benztriazolyl, indolyl or indazolyl, which may each be further substituted, for example, by $C_1$-$C_2$-alkyl or halogen.

$X_1$ and $X_2$ are different or preferably identical and are each most preferably chlorine or fluorine, in particular fluorine.

Preferred meanings of $R_2$ and $R_3$ are hydrogen or $C_1$-$C_2$-alkyl, which is unsubstituted or substituted by chlorine hydroxyl, methoxy, ethoxy, thiol, methylthio or ethylthio. Most preferred meanings of $R_2$ and $R_3$ are hydrogen, methyl, ethyl or hydroxyethyl. Preferred radicals $NR_2R_3$ are amino, methylamino, ethylamino, N,N-dimethylamino, N,N-diethylamino and N-2-hydroxyethylamino, in particular amino or N,N-dimethyl- or diethylamino.

Examples of $R_2R_3N$—$C_1$-$C_4$-alkyl are $R_2R_3N$-ethyl or, in particular $R_2R_3N$-methyl, wherein the above-given meaning and preferences apply for $R_2$ and $R_3$. Preferred $R_2R_3N$—$C_1$-$C_4$-alkyl radicals are aminomethyl, N-methylaminomethyl, N,N-dimethylaminomethyl and N,N-diethylaminomethyl.

$R_1$ as a $C_3$-$C_5$-heterocyclic radical may be, for example, any one of the above mentioned heterocyclic radicals having 3 to 5 C-atoms in its basic structure. Examples of preferred heterocyclic radicals $R_1$ are 1,3-dioxolan-2-yl, 2-methyl-1,3-dioxolan-2-yl, N-pyrrolidinyl or a radical of the formula

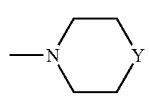

(4)

wherein Y is NH, $NC_1$-$C_2$-alkyl, O or S, preferably NH, $NCH_3$ or O, and in particular O.

Preferred radicals $R_1$ are unsubstituted or halogeno-, thiol-, $C_1$-$C_2$-alkoxy- or hydroxyl-substituted $C_1$-$C_4$-alkyl, hydroxyl, unsubstituted or halogeno-substituted $C_1$-$C_4$-alkoxy, thiol, $C_1$-$C_4$-alkylthio, halogen, $C_1$-$C_2$-alkylsulfinyl, $C_1$-$C_2$-alkylsulfonyl, $C_1$-$C_2$-alkylsulfonylamino, acetyl, acetylamino, a radical $NR_2R_3$ or $R_2R_3N$—$C_1$-$C_2$-alkyl wherein each the above-given meanings and preferences for $R_2$ and $R_3$ apply, and a radical of formula

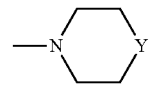

(4)

wherein Y is NH, $NC_1$-$C_2$-alkyl, O or S, preferably NH, $NCH_3$ or O, and in particular O.

Even more preferred radicals $R_1$ include unsubstituted or $C_1$-$C_2$-alkoxy- or hydroxyl-substituted $C_1$-$C_4$-alkyl, hydroxyl, unsubstituted or halogen-substituted $C_1$-$C_2$-alkoxy, $C_1$-$C_2$-alkylthio, halogen, a radical $NR_2R_3$ or $R_2R_3N$-methyl, wherein each the above-given meanings and preferences for $R_2$ and $R_3$ apply, and a radical of the above-given formula (4), wherein Y is O.

Particular preferred radicals $R_1$ include methyl, ethyl, isopropyl, 1- or 2-hydroxyethyl, hydroxyl, methoxy, ethoxy, trifluoromethoxy, methylthio, chlorine, fluorine, amino, N-mono- or N,N-dimethylamino, N-mono- or N,N-diethylamino, N-2-hydroxyethylamino, N,N-dimethylaminomethyl, N,N-diethylaminomethyl and morpholinyl.

The number of radicals $R_1$ at the phenyl ring A is from 1 to 5, preferably from 1 to 4, more preferably 1 to 3, and in particular 1 or 2. The radicals $R_1$ may be present in o-, m- and/or p-position, preferably in the m-position, relative to the C-atom which is bonded to the pyrimidine ring.

A preferred phenyl radical A is a radical of formula

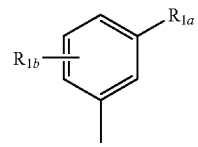

(2a)

wherein for $R_{1a}$ the meanings and preferences given above for $R_1$ apply, and $R_{1b}$ is H or has independently one the meanings given above for $R_1$. A particularly preferred embodiment of the present invention concerns a radical of the above-given formula (2a) wherein $R_{1b}$ is H, halogen, $C_1$-$C_2$-alkoxy, $C_1$-$C_2$-alkyl, halo-$C_1$-$C_2$-alkyl or halo-$C_1$-$C_2$-alkoxy, in particular H, and for $R_{1a}$ the meanings and preferences given above for $R_1$ apply. An even more preferred embodiment concerns a radical of formula (2a), wherein $R_{1b}$ is H, chlorine, fluorine, methyl, trifluoromethyl, methoxy or trifluoromethoxy, in particular H, and for $R_{1a}$ the meanings and preferences given above for $R_1$ apply.

In case A denotes a radical of formula (3), the ring (a) denotes, for example, an annulated phenyl, cyclopentyl or cyclohexyl ring which may be further substituted, for example by a substituent as given before for $R_1$. Preferably, the annulated ring (a) is a 6-membered or, in particular, a 5-membered heterocyclic ring having one or two heteroatoms selected from the group consisting of N, O and S and being unsubstituted or further substituted by $C_1$-$C_2$-alkyl. Particularly preferred annulated rings (a) are a 5-membered heterocyclic ring having 1 or 2 N- or O-atoms.

A preferred radical A is of formula

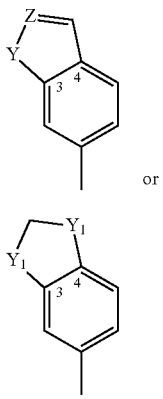

wherein Y is —NH—, —N($C_1$-$C_2$-alkyl)-, —O— or —S— and Z is CH or N, or most preferably, Y is —NH— or —N($C_1$-$C_2$-alkyl)- and Z is CH; and $Y_1$ is —O—.

In case A denotes a heterocyclic radical, said radical A is preferably a 5- or 6-membered ring having 1 or 2 same or different heteroatoms selected from the group consisting of N, O and S, which radical may be further substituted, for example, by $C_1$-$C_2$-alkyl, $C_1$-$C_2$-alkoxy or halogen, and/or may carry an annulated benzo ring. Examples of suitable heterocyclic radicals are mentioned before. Preferred heterocyclic radicals A are heteroaromatic radicals.

Examples of preferred heterocyclic radicals A are thienyl; furanyl; pyrrolyl; benzothienyl; benzofuranyl; pyrazolyl, pyridinyl; or pyrimidinyl; each of which unsubstituted or substituted, for example, by halogen or $C_1$-$C_2$-alkyl. The heterocyclic radical may be bonded via the C-atom in o- or m-position, in case of a 6-membered ring also in p-position, relative to the heteroatom. Particularly preferred heterocyclic radicals A are thien-2- or -3-yl, which is unsubstituted or substituted by methyl or chlorine; benzothien-3-yl; furan-2- or -3-yl; pyrazol-3- or -4-yl; N-methyl-pyrazol-3- or -4-yl or pyridine-3- or -4-yl.

One preferred embodiment of the present invention concerns a compound of the above-given formula (1), wherein $X_1$ and $X_2$ are each fluorine or chlorine; and A is
(i) a radical of the above-given formula (2), wherein $(R_1)_{1-5}$ is 1 to 4, preferably 1 or 2, same or different substituents selected from the group consisting of unsubstituted or halogeno-, thiol-, $C_1$-$C_2$-alkoxy- or hydroxyl-substituted $C_1$-$C_4$-alkyl; hydroxyl; unsubstituted or halogeno-substituted $C_1$-$C_4$-alkoxy; thiol; $C_1$-$C_4$-alkylthio; halogen; $C_1$-$C_2$-alkylsulfinyl; $C_1$-$C_2$-alkylsulfonyl; $C_1$-$C_2$-alkylsulfonylamino; acetyl; acetylamino; a radical $NR_2R_3$ or $R_2R_3N$—$C_1$-$C_2$-alkyl, wherein $R_2$ and $R_3$ are each independently hydrogen or $C_1$-$C_4$-alkyl which is unsubstituted or substituted by halogen, hydroxy, $C_1$-$C_4$-alkoxy, thiol or $C_1$-$C_4$-alkylthio; and a radical of the above-given formula (4), wherein Y is NH, N$C_1$-$C_2$-alkyl, O or S; or is
(ii) a radical of the above-given formula (3), wherein the annulated ring (a) is a 6-membered or, in particular, a 5-membered heterocyclic ring having one or two heteroatoms selected from the group consisting of N, O and S; or is
(iii) is a 5- or 6-membered heterocyclic radical having 1 or 2 same or different heteroatoms selected from the group consisting of N, O and S, which radical may be further substituted, for example, by $C_1$-$C_2$-alkyl, $C_1$-$C_2$-alkoxy or halogen, and/or may carry an annulated benzo ring.

A further preferred embodiment of the present invention concerns a compound of the above-given formula (1), wherein $X_1$ and $X_2$ are each fluorine; and A is
(i) a radical of the above-given formula (2a), wherein $R_{1a}$ is unsubstituted or $C_1$-$C_2$-alkoxy- or hydroxyl-substituted $C_1$-$C_4$-alkyl hydroxyl; unsubstituted or halogen-substituted $C_1$-$C_2$-alkoxy; $C_1$-$C_2$-alkylthio; halogen; a radical $NR_2R_3$ or $R_2R_3N$-methyl, wherein $R_2$ and $R_3$ are each independently hydrogen or $C_1$-$C_2$-alkyl, which is unsubstituted or substituted by chlorine hydroxyl, methoxy, ethoxy, thiol, methylthio or ethylthio; or morpholinyl; and $R_{1b}$ is H, halogen, $C_1$-$C_2$-alkoxy, $C_1$-$C_2$-alkyl, halo-$C_1$-$C_2$-alkyl or halo-$C_1$-$C_2$-alkoxy; or is
(ii) is a radical of the above-given formula (3a) or (3b), wherein Y is —NH—, —N($C_1$-$C_2$-alkyl)-, —O— or —S— and Z is CH or N; and $Y_1$ is —O—; or is
(iii) a thienyl; furanyl; pyrrolyl; benzothienyl; benzofuranyl; pyrazolyl, pyridinyl; or pyrimidinyl radical, each of which being unsubstituted or substituted, for example, by halogen or $C_1$-$C_2$-alkyl.

A particularly preferred embodiment of the present invention concerns a compound of the above-given formula (1), wherein $X_1$ and $X_2$ are each fluorine; and A is a radical of the above-given formula (2a), wherein $R_{1a}$ is methyl, ethyl, isopropyl, 1- or 2-hydroxyethyl, hydroxy, methoxy, ethoxy, trifluoromethoxy, methylthio, chlorine, fluorine, amino, N-mono- or N,N-dimethylamino, N-mono- or N,N-diethylamino, N-2-hydroxyethylamino, N,N-dimethylaminomethyl, N,N-diethylaminomethyl or morpholinyl; and $R_{1b}$ is H, chlorine, fluorine, methyl, trifluoromethyl, methoxy or trifluoromethoxy, in particular H.

Still a further preferred embodiment of the present invention concerns a compound of the above-given formula (1), wherein $X_1$ and $X_2$ are each fluorine; and A is thien-2- or -3-yl, being unsubstituted or substituted by methyl or chlorine; benzothien-3-yl; furan-2- or -3-yl; pyrazol-3- or -4-yl; N-methyl-pyrazol-3- or -4-yl or pyridine-3- or -4-yl.

The compounds of formula (1) of the present invention, in free form or in salt form respectively, may be prepared by a process for example characterized in that a compound of formula

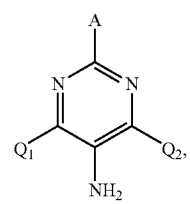

(5)

wherein A is as defined above and $Q_1$ and $Q_2$ are leaving groups, is reacted with a compound of formula

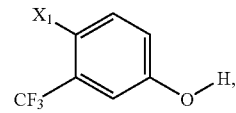

(6a)

wherein $X_1$ is as defined above, and the intermediate is reacted subsequently or at the same time with a compound of formula

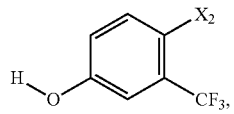

(6b)

wherein $X_2$ is as defined above,
and if desired, a compound of formula (1) obtainable according to the method or in another way, respectively in free form or in salt form, is converted into another compound of formula (1), a mixture of isomers obtainable according to the method is separated and the desired isomer isolated and/or a free compound of formula (1) obtainable according to the method is converted into a salt or a salt of an compound of formula (1) obtainable according to the method is converted into the free compound of formula (1) or into another salt.

The compounds of formula (5), (6a) and (6b) are known or may be produced analogously to known compounds.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide. Preferred is N,N-dimethylformamide, N-methylpyrrolidone or tetrahydrofuran.

Preferred leaving groups Q are halogens, especially chlorine.

Suitable bases for facilitating the reaction are e.g. alkali metal or alkaline earth metal hydroxides, hydrides, amides, alkanolates, acetates, carbonates, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Preferred is sodium hydride or potassium carbonate.

The reaction advantageously takes place in a temperature range of ca. 60° C. to ca. 120° C., preferably from ca. 80° C. to ca. 100° C.

A further preferred process for the manufacture of the compounds of formula (1) is characterized in that
(i) a compound of formula

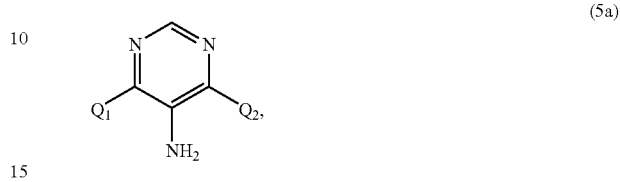

(5a)

wherein $Q_1$ and $Q_2$ are leaving groups, is first of all reacted with a compound of the above-given formula (6a) and subsequently or at the same time with a compound of the above-given formula (6b) to yield a compound of the formula

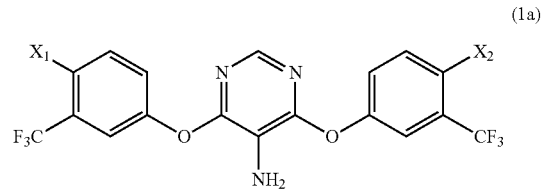

(1a)

wherein $X_1$ and $X_2$ are as defined above:
(ii) the compound of formula (1a) is then converted to a reactive derivative of the formula

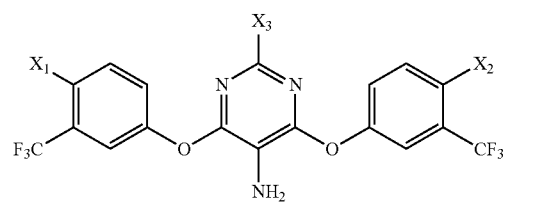

(1b)

wherein $X_1$ and $X_2$ are as defined above, and $X_3$ is, for example, halogen, in particular bromine, or is a metal derivative, e.g. $B(OH)_2$ or $Si(OEt)_3$; and
(iii) the compound of the formula (1b) is reacted with a compound of the formula

A-X$_4$     (7), wherein A is as described above and $X_4$ is a metal derivative, for example $Si(OEt)_3$ or preferably $B(OH)_2$, or is halogen, with the proviso, that one of $X_3$ and $X_4$ is halogen and the other one is a metal derivative.

The formation of the compound of formula (1a) proceeds as described above for the reaction of the compound of the formula (5) with the compounds of formula (6a) and (6b). The halogenation of the compound of formula (1a) is suitably performed according to processes known e.g. from textbooks of organic chemistry. Processes to synthesize a metal derivative of formula (1b) or (7) are likewise known to the art-skilled worker. For example, a compound of formula (1b) or (7) wherein $X_3$ or $X_4$ is halogen, in particular bromine, is metallized with an organometallic compound, for example n-butyllithium, at a low temperature, and the resulting metallorganic compound is further reacted with a boronic or silicic acid acid ester and then hydrolyzed. The coupling reaction of a compound of formula (1b) with a compound of formula (7), wherein one of $X_3$ and $X_4$ is halogen, for example bromine, and the other one is a metal derivative, for example $B(OH)_2$, is likewise known in the art (so-called Suzuki-Miyaura reaction). The step is usually performed in an aprotic solvent such as toluene with the exclusion of oxygen and may advantageously be catalyzed by a metal derivative, e.g. a Pd, Cu or Zn derivative.

Salts of compounds of Formula (1) may be produced in known manner. Acid addition salts, for example, are obtainable from compounds of the formula (1) by treating with a suitable acid or a suitable ion exchange reagent, and salts with bases are obtainable by treating with a suitable base or a suitable ion exchange reagent Salts of compounds of the formula (1) can be converted into the free compounds the formula (1) by the usual means, acid addition salts e.g. by treating with a suitable basic composition or with a suitable ion exchange reagent, and salts with bases e.g. by treating with a suitable acid or a suitable ion exchange reagent.

Salts of compounds the formula (1) can be converted into other salts of compounds the formula (1) in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds the formula (1) with salt-forming characteristics can be obtained in free form or in the form of salts.

Compounds the formula (1) can also be obtained in the form of their hydrates and/or also can include other solvents, used for example where necessary for the crystallization of compounds present in solid form.

The compounds the formula (1) may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds the formula (1), which are obtainable by the process or in another way, may be separated in known manner, on the basis of the physical-chemical differences in their components, into the pure diastereoisomers, for example by fractional crystallization, distillation and/or chromatography.

Splitting of mixtures of enantiomers that are obtainable accordingly may be achieved by known methods, for example by recrystallization from an optically active solvent, by chromatography on chiral adsorbents, e.g. high-pressure liquid chromatography (HPLC) on acetyl cellulose, with the assistance of appropriate micro-organisms, by cleavage with specific immobilized enzymes, through the formation of inclusion compounds, e.g. using chiral crown ethers, whereby only one enantiomer is complexed.

According to the invention, apart from separation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesize the biologically more active isomer, e.g. enantiomer, provided that the individual components have differing biological efficacy.

The compounds of the formula (1) according to the invention are notable for their broad activity spectrum and are valuable active ingredients for use in pest control. They are particularly suitable in the control of ectoparasites and to a certain extent also for controlling endoparasites on and in animals and in the hygiene field, whilst being well tolerated by warm-blooded animals.

In the context of the present invention, ectoparasites are understood to be in particular insects, acari (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericata, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys calcitrans*, horse-flies (Tabanids) with the subfamilies of Tabanidae such as *Haematopota* spp. (e.g. *Haematopota pluvialis*) and *Tabanus* spp, (e.g. *Tabanus nigrovittatus*) and Chrysopsinae such as *Chrysops* spp. (e.g. *Chrysops caecutiens*); Hippoboscids such as *Melophagus ovinus* (sheep ked); tsetse flies, such as *Glossinia* spp,; other biting insects like midges, such as Ceratopogonidae (biting midges), Simuliidae (Blackflies), Psychodidae (Sandflies); but also blood-sucking insects, for example mosquitoes, such as *Anopheles* spp, *Aedes* spp and *Culex* spp, fleas, such as *Ctenocephalides felis* and *Ctenocephalides canis* (cat and dog fleas), *Xenopsylla cheopis, Pulex irritans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (Mallophaga) such as *Bovicola* (Damalinia) *ovis, Bovicola* (Damalinia) *bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes ovis* and *Psorergates* spp. and ticks. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, horses, pigs, sheep and goats, poultry such as chickens, turkeys, guineafowls and geese, fur-bearing animals such as mink, foxes, chinchillas, rabbits and the like, as well as companion animals such as ferrets, guinea pigs, rats, hamster, cats and dogs, but also humans.

The compounds of the formula (1) according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds of the formula (1) can also be used against hygiene pests, especially of the order Diptera of the families Muscidae, Sarcophagidae, Anophilidae and Culicidae; the orders Orthoptera, Dictyoptera (e.g. the family Blattidae (cockroaches), such as *Blatella germanica, Blatta orientalis, Periplaneta americana*) and Hymenoptera (e.g. the families Formicidae (ants) and Vespidae (wasps).

Surprisingly, the compounds of formula (1) are also effective against ectoparasites of fishes, especially the sub-class of Copepoda (e.g. order of Siphonostognatoidae (sea lice), whilst being well tolerated by fish.

Certain compounds of the formula (1) seem to be also effective against certain species of helminths.

Helminths are commercially important because they cause serious diseases in mammals and poultry, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are: *Haemonchus, Trichostrongylus, Ostertagia, Nematodirus, Cooperia, Ascaris, Bunostomum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica*.

The good pesticidal activity of the compounds of formula (1) according to the invention corresponds to a mortality rate of at least 50-60% of the pests mentioned, more preferably to a mortality rate over 90%, most preferably to 95-100%. The compounds of formula (1) are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e.g. capsules, powders including soluble powders, granules, or embeddings of the active ingredient in polymeric substances, like implants and microparticles). As with the compositions, the methods of application are selected in accordance with the intended objectives and the prevailing circumstances.

The formulation, i.e. preparations containing the active ingredient of formula (1), or combinations of these active ingredients with other active ingredients, and optionally a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, carbonates, such as propylene carbonate, ketones, such as cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpalmitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application forms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholestesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™, saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers, polyvinyl alcohols, polyvinylpyrrolidons and fine disperse silicium dioxide.

As polymeric agents with controlled release properties, may be applied derivatives made by e.g. polylactic acid, polylactic coglycolic acid, poly orthoester, polyethylene carbonate, poly anhydrids and starch and PVC based matrices.

The addition of penetration enhancers like ketones, sulfoxides, amides, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may also applied in capsules, like hard gelatine capsules or soft capsules.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), lubricants (e.g. magnesium stearate), glidants (e.g. colloidal silicon dioxide) and disintegrants (e.g. cellulose derivatives) and acid resistant coatings, like e.g. acrylic acid esters.

The compounds of formula (1) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. Since the compounds of formula (1) are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (1).

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers. Non-limitative examples of suitable insecticides and acaricides are disclosed, for example, in WO 2005/058802 on pages 13-15, No. 1. to 185. Non-limitative examples of suitable anthelminthics are named, for example, in WO 2005/058802 on page 16, Nrs. (A1) to (A12). Non-limitative examples of suitable repellents and detachers are: (i) DEET (N,N-diethyl-m-toluamide), (ii) KBR 3023 N-butyl-2-oxycarbonyl-(2-hydroxy)-piperidine, and (iii) Cymiazole=N,-2,3-dihydro-3-methyl-1,3-thiazol-2-ylidene-2,4-xylidene.

The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. A list of suitable partners including a reference is disclosed in WO 2005/058802 on pages 16-21, No. (I) to (CLXXXIII).

As a consequence of the above details, a further aspect of the present invention relates to a combination preparation for the control of parasites on warm-blooded animals, characterized in that it contains, in addition to a compound of formula (1), at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of one or more active ingredients of formula (1), 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present, for example, in the form of solutions, emulsions, suspensions, (drenches), powders, tablets, boli, capsules, collars, eartags and pour-on formulations.

Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to 1 ml per kg, preferably about 0.1 ml per kg, with a total volume from 0.1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidized form. Paraffins and silicone oils may also be used.

A pour-on or spot-on formulation generally contains 1 to 98.9% by weight of a compound of formula (1), 0.1 to 80% by weight of dispersing agent and 1 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates.

Such compositions may also contain further additives, such as stabilizers, anti-foaming agents, viscosity regulators, binding agents or tackifiers, as well as other active ingredients, in order to achieve special effects.

Insecticidal and acaricidal compositions of this type, which are used by the end user, similarly form a constituent of the present invention.

In each of the processes according to the invention for pest control or in each of the pest control compositions according to the invention, the active ingredients of formula (1) can be used in all of their steric configurations or in mixtures thereof.

The invention also includes a method of prophylactically protecting animals, especially productive livestock, domestic animals and pets, against parasitic helminths, which is characterized in that the active ingredients of formula (1) or the active ingredient formulations prepared therefrom are administered to the animals as an additive to the feed, or to the drinks or also in solid or liquid form, orally or by injection or parenterally. The invention also includes the compounds of formula (1) according to the invention for usage in one of the said processes.

The following examples serve merely to illustrate the invention without restricting it, the term active ingredient representing any substance as described in the preparation examples.

In particular, preferred formulations are made up as follows: (%=percent by weight)

FORMULATION EXAMPLES

1. Granulate

|  | a) | b) |
|---|---|---|
| (i) active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

| (ii) active ingredient | 3% |
|---|---|
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

2. Tablets or Boli

| I | active ingredient | 33.00% |
|---|---|---|
|  | methylcellulose | 0.80% |
|  | silicic acid, highly dispersed | 0.80% |
|  | corn starch | 8.40% |
| II | lactose, cryst. | 22.50% |
|  | corn starch | 17.00% |
|  | microcryst. cellulose | 16.50% |
|  | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

3. Injectables

A. Oily Vehicle (Slow Release)

| (i) active ingredient | 0.1-1.0 g |
|---|---|
| groundnut oil | ad 100 ml |
| (ii) active ingredient | 0.1-1.0 g |
| sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 µm.

B Water-Miscible Solvent (Average Rate of Release)

| (i) active ingredient | 0.1-1.0 g |
|---|---|
| 4-hydroxymethyl-1,3-dioxolane (glycerol formal) | 40 g |
| 1,2-propanediol | ad 100 ml |
| (ii) active ingredient | 0.1-1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 µm.

C. Aqueous Solubilizate (Rapid Release)

| (i) active ingredient | 0.1-1.0 g |
|---|---|
| polyethoxylated castor oil (40 ethylene oxide units) | 10 g |
| 1,2-propanediol | 20 g |
| benzyl alcohol | 1 g |
| aqua ad inject. | ad 100 ml |
| (ii) active ingredient | 0.1-1.0 g |
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| aqua ad inject. | ad 100 ml |

Preparation: The active ingredient is dissolved in the solvents and the surfactant, and made up with water to the desired volume. Sterile filtration through an appropriate membrane filter of 0.22 µm pore size.

4. Pour On

| (i) active ingredient | 5 g |
|---|---|
| isopropyl myristate | 10 g |
| isopropanol | ad 100 ml |
| (ii) active ingredient | 2 g |
| hexyl laurate | 5 g |
| medium-chained triglyceride | 15 g |
| ethanol | ad 100 ml |
| (iii) active ingredient | 2 g |
| oleyl oleate | 5 g |
| N-methyl-pyrrolidone | 40 g |
| isopropanol | ad 100 ml |

5. Spot On

|     |                              |            |
| --- | ---------------------------- | ---------- |
| (i) | active ingredient            | 10-15 g    |
|     | diethyleneglycol monoethylether | ad 100 ml |
| (ii) | active ingredient            | 10-15 g    |
|     | octyl palmitate              | 10 g       |
|     | isopropanol                  | ad 100 ml  |
| (iii)| active ingredient            | 10-15 g    |
|     | isopropanol                  | 20 g       |
|     | benzyl alcohol               | ad 100 ml  |

6. Spray On

|     |                     |           |
| --- | ------------------- | --------- |
| (i) | active ingredient   | 1 g       |
|     | isopropanol         | 40 g      |
|     | propylene carbonate | ad 100 ml |
| (ii)| active ingredient   | 1 g       |
|     | propylene glycol    | 10 g      |
|     | isopropanol         | ad 100 ml |

The aqueous systems may also preferably be used for oral and/or intraruminal application.

The compositions may also contain further additives, such as stabilizers, e.g. where appropriate epoxidized vegetable oils (epoxidized coconut oil, rapeseed oil, or soybean oil); antifoams, e.g. silicone oil, preservatives, viscosity regulators, binders, tackifiers, as well as fertilizers or other active ingredients to achieve special effects.

Further biologically active substances or additives, which are neutral towards the compounds of formula (1) and do not have a harmful effect on the host animal to be treated, as well as mineral salts or vitamins, may also be added to the described compositions.

The following examples serve to illustrate the invention. They do not limit the invention. The letter 'h' stands for hour. The starting materials are known and partially commercially available or may be produced in analogy to methods known per se.

PREPARATION EXAMPLES

Example 1

4,6-bis-(4-fluoro-3-(trifluoromethyl)phenoxy)-pyrimidin-5-ylamine

Dissolved in 70 ml DMF, 40.8 g 4-fluoro-3-(trifluoromethyl)-phenol are stirred under an inert gas atmosphere and cooled to 10° C. To this, 5.8 g sodium hydride are added slowly under vigorous stirring. The mixture is then allowed to warm up to room temperature and stirred for 1 h. Then, a solution of 19.9 g 4,6-Dichloro-5-aminopyrimidine in 50 ml DMF is added dropwise and the reaction mixture is heated for 24 h at 80° C. After quenching with water and concentration under reduced pressure the crude mixture is extracted twice with ethyl acetate. The combined organic phases are washed with water and saturated sodium chloride and finally dried over magnesium sulfate and charcoal. The dark brown oily residue is dissolved in 100 ml diethylether and treated with 100 ml hexane. The resulting title compound crystallizes as a colorless solid with a melting point of 104-105° C.

Example 2

2-Bromo-4,6-bis-(4-fluoro-3-trifluoromethyl-phenoxy)-pyrimidin-5-ylamine 3.9 ml bromine in 50 ml acetic acid are added dropwise to a solution of 34 g of 4,6-bis-(4-fluoro-3-(trifluoromethyl)phenoxy)-pyrimidin-5-ylamine in 150 ml acetic acid under nitrogen. The mixture is stirred overnight at room temperature. 2 ml of bromine in 25 ml acetic acid are added dropwise. The mixture is stirred overnight at room temperature and is then poured over 2.5 l ice/water. The precipitate is collected by filtration, dissolved in 400 ml dichloromethane, and washed with water. The organic layer is dried over $MgSO_4$, filtered and then concentrated under vacuum to give 29 g of a brown solid. The solid is further purified by filtration over silica gel and recrystallization from diisopropylether to give 23 g of 2-Bromo-4,6-bis-(4-fluoro-3-trifluoromethyl-phenoxy)-pyrimidin-5-ylamine (mp. 184-186° C.).

Example 3

2-(3-Dimethylamino-phenyl)-4,6-bis-(4-fluoro-3-trifluoromethyl-phenoxy)-pyrimidin-5-ylamine 23 g of 2-Bromo-4,6-bis-(4-fluoro-3-trifluoromethyl-phenoxy)-pyrimidin-5-ylamine are dissolved under nitrogen together with 10.7 g of 3-(N,N-dimethylamino)phenylboronic acid, 0.4 g of tris(dibenzylideneacetone)dipalladium, 27.5 g of $K_3PO_4$ and 0.7 g of 2-dicyclohexyl-phosphino-2', 6'-dimethoxybiphenyl in 450 ml of toluene. The mixture is heated at 75° C. for 24 h, diluted with diethylether, washed with water and then dried over $MgSO_4$. The solvents are removed under vacuum. 14.8 g of the title compound are isolated as white powder (mp. 110-111° C.) after purification by filtration and recrystallization from cyclohexane.

The substances named in the following Tables 1, 1a, 1b, 2, 2a and 2b are prepared analogously to the above-described method.

Table 1 provides 34 compounds of formula

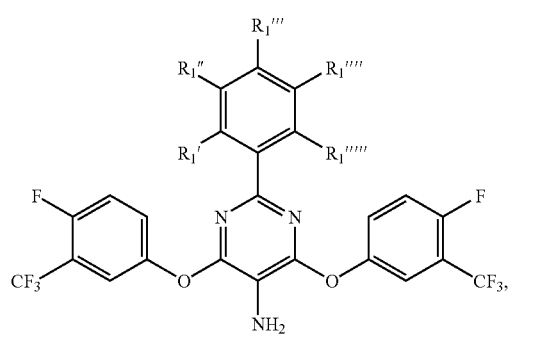

(1')

wherein the meanings of $R_1'$, $R_1''$, $R_1'''$, $R_1''''$ and $R_1'''''$ are given in Table 1.

TABLE 1

| No | R₁' | R₁" | R₁'" | R₁"" | R₁""' | mp (°C.) |
|---|---|---|---|---|---|---|
| 1.1 | H | H | CF₃ | H | H | 128-129 |
| 1.2 | H | H | OCH₃ | H | H | 158-160 |
| 1.3 | H | H | Cl | H | H | 156-158 |
| 1.4 | H | Cl | H | H | H | 142-144 |
| 1.5 | Cl | H | H | H | H | 106-109 |
| 1.6 | OCH₃ | H | H | H | H | 128-130 |
| 1.7 | H | OCH₃ | H | H | H | 110-112 |
| 1.8 | H | Cl | H | Cl | H | 157-160 |
| 1.9 | H | CH₃ | H | H | H | 128-130 |
| 1.10 | H | CH(CH₃)₂ | H | H | H | 79-81 |
| 1.11 | H | S—CH₃ | H | H | H | 89-91 |
| 1.12 | H | OCH₃ | H | OCH₃ | H | 143-144 |
| 1.13 | H | F | H | H | H | 113-115 |
| 1.14 | H | C(O)CH₃ | H | H | H | 140-141 |
| 1.15 | H | OCF₃ | H | H | H | 142-143 |
| 1.16 | H | S(O)CH₃ | H | H | H | 155-156 |
| 1.17 | H | S(O)₂CH₃ | H | H | H | 140-142 |
| 1.18 | H | CH(OH)CH₃ | H | H | H |  |
| 1.19 | H | NHC(O)CH₃ | H | H | H | 205-206 |
| 1.20 | H | OH | H | H | H | 173-175 |
| 1.21 | H | NHS(O)₂CH₃ | H | H | H | 151-153 |
| 1.22 | F | H | H | H | F | 79-81 |
| 1.23 | H | CH₃ | F | H | H | 130-132 |
| 1.24 | H | 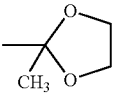 | H | H | H | 142-144 |
| 1.25 | H | OCH₃ | H | H | F | 85-87 |
| 1.26 | H | NH₂ | H | H | H | 128-129 |
| 1.27 | H | CH₂OCH₃ | H | H | H | 116-118 |
| 1.28 | H | CH₂N(CH₃)₂ | H | H | H |  |
| 1.29 | H | N(CH₃)₂ | F | H | H |  |
| 1.30 | H | 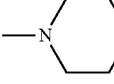 | H | H | H | 149-150 |
| 1.31 | H | 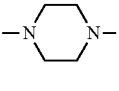 | H | H | H |  |
| 1.32 | H | 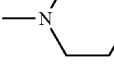 | H | H | H | 118-119 |
| 1.33 | H | 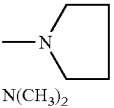 | H | H | H | 104-105 |
| 1.34 | H | N(CH₃)₂ | H | H | H | 110-111 |

Table 1a provides 34 compounds of formula

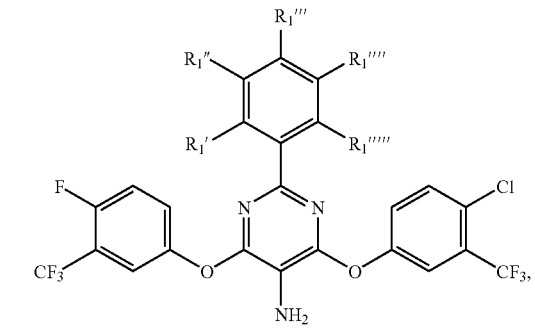

(1″)

wherein the meanings of R₁', R₁", R₁'", R₁"" and R₁""' are given in Table 1.

Table 1b provides 34 compounds of formula

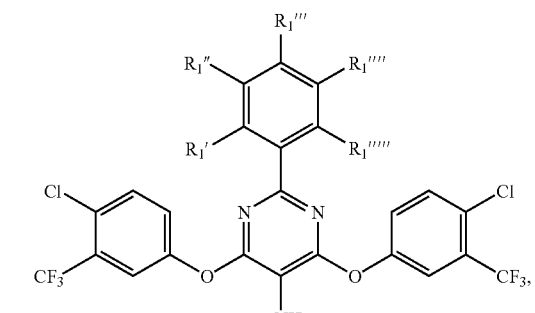

(1‴)

wherein the meanings of R₁', R₁", R₁'", R₁"" and R₁""' are given in Table 1.

Table 2 provides 12 compounds of formula

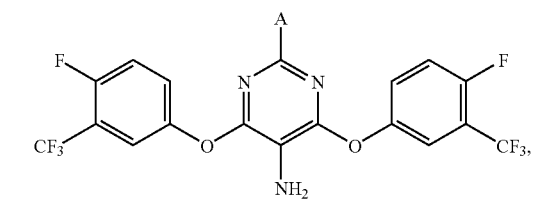

(1*)

wherein the meaning of A is given in Table 2.

TABLE 2

| No | A | mp (°C.) |
|---|---|---|
| 2.1 | 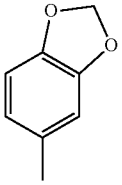 | 128-129 |

TABLE 2-continued

| No | A | mp (° C.) |
|---|---|---|
| 2.2 | 3-methyl-1-methylindol-? | 122-124 |
| 2.3 | 6-methylindole | |
| 2.4 | 3-methylfuran | 99-102 |
| 2.5 | 5-chloro-2-methylthiophene | 106-108 |
| 2.6 | 3-methylthiophene | 108-111 |
| 2.7 | 3-methylbenzothiophene | 127-129 |
| 2.8 | 3-methyl-5-methylthiophene | 100-102 |
| 2.9 | 2-methylfuran | 128-130 |
| 2.10 | 3-methylpyridine | 124-125 |
| 2.11 | 4-methylpyridine | 170-171 |
| 2.12 | 1,4-dimethylpyrazole | 138-140 |

Table 2a provides 12 compounds of formula

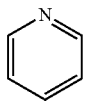

(1**)

wherein the meaning of A is given in Table 2.
Table 2b provides 12 compounds of formula

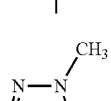

(1***)

wherein the meaning of A is given in Table 2.

BIOLOGICAL EXAMPLES

1. Activity in Vitro Against *Dermanyssus gallinae* (Chicken Red Mite)—High Throughput Screening (HTS)

A clean female mite population is used to seed a suitably formatted 96-well plate containing the test substances to be evaluated for antiparasitic activity. Each compound is tested by serial dilution in order to determine its Minimal Effective Dose (MED). Mites are left in contact with the test compound for 10 minutes and are then incubated at 25° C. and 60% relative humidity (RH) for 5 days, during which the test compound's effect is monitored. Acaricidal activity is confirmed if mites are dead without having laid eggs. Egg-laying and ensuing mite development are also recorded to identify possible growth-regulating activity.

The compounds number 1.3, 1.4, 1.7, 1.8, 1.9, 1.10, 1.11, 1.12, 1.13, 1.14, 1.15, 1.23, 1.25, 1.27, 1.30, 1.32, 1.33, 1.34, 2.1, 2.2, 2.3, 2.4, 2.5, 2.6, 2.7, 2.8 and 2.12 all show in the HTS efficacy of more than 60% at 200 ppm.

2. Activity in Vitro Against *Rhipicephalus sanguineus* (Dog Ticks)—HTS

A clean adult tick population is used to seed a suitably formatted 96-well plate containing the test substances to be evaluated for antiparasitic activity. Each compound is tested by serial dilution in order to determine its MED. Ticks are left in contact with the test compound for 10 minutes and are then incubated at 28° C. and 80% relative humidity (RH) for 7 days, during which the test compound's effect is monitored. Acaricidal activity is confirmed if and when adult ticks are dead.

The compounds number 1.2, 1.4, 1.7, 1.9, 1.10, 1.11, 1.12, 1.13, 1.14, 1.18, 1.23, 1.25, 1.27, 1.30, 1.32, 1.33, 1.34, 2.1, 2.2, 2.3, 2.4, 2.5, 2.7, 2.8 and 2.9 all show in the HTS efficacy of more than 60% at 640 ppm. By contrast, the compound 2-phenyl-4,6-bis-(4-fluoro-3-[trifluoromethyl]phenoxy)-5-amino-pyrimidine known from WO 2005/85211 does not show any significant acaricidal efficacy in this test.

3. Activity in Vitro Against *Ctenocephalides felis* (Cat Flea)—HTS

A mixed adult population of fleas is placed in a suitably formatted 96-well plate allowing fleas to access and feed on treated blood via an artificial feeding system. Each compound is tested by serial dilution in order to determine its MED. Fleas are fed on treated blood for 24 hours, after which the compound's effect is recorded. Insecticidal activity is determined on the basis of the number of dead fleas recovered from the feeding system.

The compounds number 1.7, 1.11, 1.18, 1.21, 1.32, 1.33, 1.34, 2.1, 2.2, 2.3, 2.4, 2.6 and 2.7 all show in the HTS insecticidal efficacy of more than 60% at 100 ppm. By contrast, the compound 2-phenyl-4,6-bis-(4-fluoro-3-[trifluoromethyl]phenoxy)-5-amino-pyrimidine known from WO 2005/85211 does not show any significant insecticidal efficacy in this test.

4. In-Vivo Test Against *Rhipicephalus sanquineus* Nymphs on Mongolian Gerbils (*Meriones unguiculatus*)

On day 0, gerbils are treated with the test compound at a given dose by spray (or spot-on) application. On day +1 (+2), the animals are infested with nymphs of *R. sanguineus*. Ticks are left on the animals until full repletion. Seven days after infestation nymphs dropped off fully engorged are collected and counted. They are kept until molting to also evaluate growth regulating activity of the test compound. Efficacy in killing (and growth regulating) is expressed as a tick number (and molted tick number) reduction in comparison with a placebo treated group, using the Abbot's formula. A tick number reduction of more than 60%, in particular more than 70%, is regarded as a minimum prerequisite for a commercial development of a compound. In addition, said killing efficacy should be put into practice with the minimal dose for safety and environmental reasons.

| Compound | Dose [mg/kg] | % reduction of number of ticks |
|---|---|---|
| 1.7 | 3.2 | 91 |
| 1.9 | 10 | 74 |
| 1.10 | 10 | 81 |
| 1.18 | 10 | 85 |
| 1.23 | 10 | 99 |
| 1.27 | 3.2 | 78 |
| 1.30 | 3.2 | 79 |
| 1.34 | 3.2 | 85 |
| 2.2 | 3.2 | 89 |
| 2.3 | 3.2 | 81 |

No significant killing efficacy was observed with the compound 2-phenyl-4,6-bis-(4-fluoro-3-[trifluoromethyl]phenoxy)-5-amino-pyrimidine known from WO 2005/85211 at these low concentrations.

The invention claimed is:

1. A compound of formula (1)

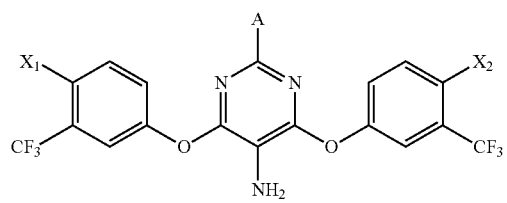

(1)

wherein $X_1$ and $X_2$ are each independently halogen; and A is a radical of formula (2a)

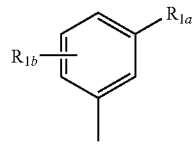

(2a)

wherein $R_{1a}$ is methyl, ethyl, isopropyl, 1- or 2-hydroxyethyl, hydroxy, methoxy, ethoxy, trifluoromethoxy, methylthio, chlorine, fluorine, amino, N-mono- or N,N-dimethylamino, N-mono- or N,N-diethylamino, N-2-hydroxyethylamino N,N-dimethylaminomethyl, N,N-diethylaminomethyl, or morpholinyl, and $R_{1b}$ is H, halogen, $C_1$-$C_2$-alkoxy, $C_1$-$C_2$-alkyl, halo-$C_1$-$C_2$-alkyl or halo-$C_1$-$C_2$-alkoxy; in free form or in salt form.

2. The compound of formula (1) according to claim 1, wherein $X_1$ and $X_2$ are each fluorine.

3. The compound of formula (1) according to claim 2, wherein $R_{1b}$ is H.

4. The compound of formula (1) according to claim 2, wherein $R_{1a}$ is amino, N-mono- or N,N-dimethylamino, N-mono- or N,N-diethylamino or N-2-hydroxyethylamino, and $R_{1b}$ is H.

5. The compound of formula (1) according to claim 1, which is 2-(3-Dimethylamino-phenyl)-4,6-bis-(4-fluoro-3-trifluoromethyl-phenoxy)-pyrimidin-5-ylamine.

6. A method of controlling parasites in and on warm-blooded animals, comprising applying to an animal a pharmaceutical effective amount of at least one compound of claim 1.

* * * * *